(12) United States Patent
Shin et al.

(10) Patent No.: US 9,581,586 B2
(45) Date of Patent: Feb. 28, 2017

(54) APPROACH TO ASTHMA INHALER COMPLIANCE USING BREATH MEASUREMENT OF TETRAFLUOROETHANE

(71) Applicant: The Regents of the University of California, Oakland, CA (US)

(72) Inventors: Hye-Won Shin, Irvine, CA (US); Dan M. Cooper, Irvine, CA (US); Donald R. Blake, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 102 days.

(21) Appl. No.: 14/712,280

(22) Filed: May 14, 2015

(65) Prior Publication Data

US 2015/0330964 A1 Nov. 19, 2015

Related U.S. Application Data

(60) Provisional application No. 61/994,814, filed on May 16, 2014.

(51) Int. Cl.
*G01N 33/497* (2006.01)
*A61B 5/08* (2006.01)
(Continued)

(52) U.S. Cl.
CPC ........... *G01N 33/497* (2013.01); *A61B 5/082* (2013.01); *A61B 5/4848* (2013.01);
(Continued)

(58) Field of Classification Search
CPC ......... A61B 5/082; A61B 5/08; A61B 5/4848; A61B 5/097; A61M 15/00; A61M 2230/43;
(Continued)

(56) References Cited

U.S. PATENT DOCUMENTS 5,505,192 A * 4/1996 Samiotes ............ A61M 15/008
128/200.14
5,676,129 A * 10/1997 Rocci, Jr. ............ A61M 15/009
128/200.14
(Continued)

OTHER PUBLICATIONS

Apter et al., Problem Solving To Improve Adherence and Asthma Outcomes In Urban Adults With Moderate Or Severe Asthma: A Randomized Controlled Trial, Journal of Allergy and Clinical Immunology (Sep. 2011), pp. 516-523, 128(3).
(Continued)

*Primary Examiner* — Laura Martin
*Assistant Examiner* — Irving A Campbell
(74) *Attorney, Agent, or Firm* — Archer Norris, PLC; Sean D. Senn; Priti D. Phukan (57) ABSTRACT

The invention relates to measuring the effectiveness and an compliance of inhaler medication, such as for asthma treatment. In one embodiment, the invention provides a method of determining the effectiveness of an inhaler medication, comprising taking a measurement of HFA-134(a) from an exhaled breath of an individual after the individual has inhaled a medication, and determining an effective administration of the medication based on the presence of a high level of HFA-134(a).

21 Claims, 8 Drawing Sheets

(51) Int. Cl.
A61B 5/00 (2006.01)
G01N 30/72 (2006.01)
A61B 5/097 (2006.01)
A61M 15/00 (2006.01)

(52) U.S. Cl.
CPC .......... *G01N 30/7206* (2013.01); *A61B 5/097* (2013.01); *A61M 15/00* (2013.01); *A61M 2230/43* (2013.01); *G01N 2033/4975* (2013.01)

(58) Field of Classification Search
CPC ............. G01N 30/7206; G01N 33/497; G01N 2033/4975
USPC .......................................... 73/23.3
See application file for complete search history.

(56) References Cited

U.S. PATENT DOCUMENTS

| | | | | |
|---|---|---|---|---|
| 6,202,642 B1* | 3/2001 | McKinnon | .......... | A61M 15/009 128/200.14 |
| 8,807,131 B1* | 8/2014 | Tunnell | ............. | A61M 16/0051 128/200.14 |
| 2007/0258909 A1* | 11/2007 | Mahaut | .................. | G01N 30/88 424/40 |

OTHER PUBLICATIONS

Bender et al., Nonadherence In Asthmatic Patients: Is There A Solution To The Problem?, Annals of Allergy, Asthma & Immunology (Sep. 1997), pp. 177-186, 79.

Chan et al., Adherence Monitoring and E-Health: How Clinicians and Researchers Can Use Technology To Promote Inhaler Adherence for Asthma, The Journal of Allergy and Clinical Immunology: In Practice (Sep./Oct. 2013), pp. 446-454, 1(5).

Gamble et al., The Prevalence of Nonadherence in Difficult Asthma, American Journal of Respiratory and Critical Care Medicine (Nov. 1, 2009), pp. 817-822, 80(9).

Gunnare et al., Experimental Exposure To 1,1,1-trifluoroethane (HFC-143a): Uptake, Disposition and Acute Effects In Male Volunteers, Toxicology Letters (2007), pp. 120-130, 172.

Gunnare et al., Toxicokinetics of 1,1,1,2-tetrafluoroethane (HFC-134a) In Male Volunteers After Experimental Exposure, Toxicology Letters (2006), pp. 54-65, 167.

Harrison et al., Twenty-Eight-Day Double-Blind Safety Study of an HFA-134a Inhalation Aerosol System In Healthy Subjects, Journal of Pharmacy and Pharmacology (Jun. 1996), pp. 596-600, 48(6).

Hawkins et al., Stepping Down Inhaled Corticosteroids In Asthma: Randomised Controlled Trial, BMJ (May 24, 2003), pp. 1115-1121, 326(7399).

Monte et al., The Minimal Metabolism Of Inhaled 1,1,1,2-Tetrafluoroethane To Trifluoroacetic Acid In Man As Determined By High Sensitivity 19F Nuclear Magnetic Resonance Spectroscopy Of Urine Samples, Journal of Pharmaceutical & Biomedical Analysis (1994), pp. 1489-1493, 12(12).

Patel et al., Accuracy Of Patient Self-Report As A Measure Of Inhaled Asthma Medication Use, Respirology (2013), pp. 546-552, 18(3).

Pedersen et al., A Comparison Of The Efficacy and Safety Of Inhaled Corticosteroids In Asthma, Allergy (1997), pp. 1-34, 52(Suppl. 39).

Pike et al., Disposition Of Inhaled 1,1,1,2-TetraFluoroethane (HFA134A) In Healthy Subjects and In Patients With Chronic Airlfow Limitation: Measurement By 18F-Labelling and Whole-Body γ-Counting, Drug Metabolism and Disposition (Aug. 1995), pp. 832-839, 23(8).

Suissa et al., Regular Use Of Inhaled Corticosteroids and The Long-Term Prevention of Hospitalization For Asthma, Thorax (Oct. 2002), pp. 880-884, 57(10).

Williams et al., Quantifying The Proportion Of Severe Asthma Exacerbations Attributable To Inhaled Corticosteroid Non-Adherence, The Journal of Allergy and Clinical Immunology (Dec. 2011), pp. 1185-1191, 128(6).

* cited by examiner

APPROACH TO ASTHMA INHALER COMPLIANCE USING BREATH MEASUREMENT OF TETRAFLUOROETHANE

CROSS-REFERENCE TO RELATED APPLICATIONS

The present application claims the benefit of priority under 35 U.S.C. §119(e) of provisional application Ser. No. 61/994,814, filed May 16, 2014, the contents of which are hereby incorporated by reference.

GOVERNMENT RIGHTS

The U.S. Government has a paid-up license in this invention and the right in limited circumstances to require the patent owner to license others on reasonable terms as provided for by the terms of Grant Nos. P01 HD048721 and UL1 RR031985 awarded by the National Institutes of Health.

FIELD OF INVENTION

The invention relates to the field of medicine, and more specifically, to medical devices related to inhaler medications and treatments.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Asthma inhalers (i.e., inhaled corticosteroids) are the first line of asthma treatment. However, one of the most vexing problems facing clinicians and researchers has been the lack of technologies to measure treatment compliance and/or efficacy. The typical methods to measure ICS compliance— patient self-report of medication use and medication canister weighing or counting actuations are not optimal for both adults and children. Patient self-report of asthma inhaler use is notoriously inaccurate. Other advanced methods such as electronic monitoring of ICS compliance are limited because it will not be able to detect whether the medication is actually inhaled. Thus, there is a need in the art for a readily accessible method to identify asthma inhaler compliance or treatment efficacy.

SUMMARY OF THE INVENTION

Various embodiments herein include a method of determining the effectiveness of an inhaler medication, comprising taking a measurement of HFA-134(a) from an exhaled breath of an individual after the individual has inhaled a medication, and determining an effective administration of the medication based on the presence of a high level of HFA-134(a). In another embodiment, the individual is being treated for asthma. In another embodiment, the medication is a cortico steroid. In another embodiment, the medication is a short acting bronchodilator. In another embodiment, the medication is Flovent HFA or Proventil HFA. In another embodiment, the medication is a β2 agonist. In another embodiment, the measurement of HFA-134(a) is taken within 24 hours of inhaling the medication. In another embodiment, the measurement of HFA-134(a) is taken between 5 and 12 hours of inhaling the medication. In another embodiment, the measurement of HFA-134(a) is taken between 24 and 48 hours of inhaling the medication. In another embodiment, the high level of HFA-134(a) is at or above $300 \times 10^6$ pptv HFA-134(a) levels. In another embodiment, the high level of HFA-134(a) is an at least $10^6$ order of magnitude increase relative to normal levels. In another embodiment, the high level of HFA-134(a) is an at least $10^3$ order of magnitude increase relative to ambient levels of HFA-134(a). In another embodiment, the high level of HFA-134(a) is an at least $10^2$ order of magnitude increase relative to ambient levels of HFA-134(a). In another embodiment, the high level of HFA-134(a) is between 3 to 300 ppmv from measurements taken immediately after inhaling the medication. In another embodiment, the high level of HFA-134(a) is about 260(138) pptv or more in exhaled breath. In another embodiment, the measurement of HFA-134(a) in exhaled breath is taken within 48 hours of inhaling the medication.

Other embodiments include a device, comprising an analytic system that can take a measurement of HFA-134(a) from an exhaled breath of an individual after the individual has inhaled a medication, take a measurement and quantify a corresponding ambient level of HFA-134(a), and determine whether there has been an effective administration of the medication based on the presence of a high level of HFA-134(a) relative to the corresponding ambient level of HFA-134(a). In another embodiment, the HFA-134(a) levels are measured and quantified using a mass spectrometer detector (MSD). In another embodiment, the device further comprises gas chromatography and mass spectrometry.

Other embodiments include a method to determine compliance and treatment efficacy with inhalers, comprising examining hydrofluoroalkane (HFA) in the exhaled human breath as a biomarker of asthma inhaler compliance. In another embodiment, the method further comprises two components: 1) analytical technique to measure breath HFA in a range of parts-permillion (ppbv) to parts-per-trillion (pptv) using gas chromatography and mass spectrometry and 2) multi-compartmental analysis of HFA biotransport in the human airway following inhaled doses of ICS to estimate HFA elimination pharmacokinetic parameters such as rate constants.

Other features and advantages of the invention will become apparent from the following detailed description, taken in conjunction with the accompanying drawings, which illustrate, by way of example, various embodiments of the invention.

BRIEF DESCRIPTION OF FIGURES

Exemplary embodiments are illustrated in referenced figures. It is intended that the embodiments and figures disclosed herein are to be considered illustrative rather than restrictive.

FIG. 1 depicts, in accordance with an embodiment herein, HFA-134a levels. The figure depicts HFA-134a levels (mixing ratios on log scale) measured over a 48 hours period in the exhaled breath of healthy subjects who took (A) Flovent HFA (in red) and (B) Proventil HFA (in blue). Closed circles represent exhaled breath HFA-134 levels and open circles represent corresponding room HFA-134a levels. *The mixing ratio of HFA-134a is the ratio of the number density of HFA-134a to the total number density of air. Or, in other words, is the ratio of the number of molecule of HFA-134a in a unit volume to the number of molecule of air in a unit volume. (C) baseline HFA levels from control participants blue closed circle, black bar represents mean value) and a symptomatic asthma (n=1, red closed circle) who was on nine day ICS treatment prior to the study participation. The asthma participant took ICS approximately 24 hr prior to the study participation. As shown in FIG. 1, baseline HFA level from a symptomatic asthma was ~15-fold higher (710 ppt) when compared to the mean HFA levels obtained from control participants (47 pptv).

$$C_{HFA-134a}=1000(Amb+A_1 \cdot e^{(L_1 \cdot t)}+A_2 \cdot e^{(L_2 \cdot t)}+A_3 \cdot e^{(L_3 \cdot t)}) \quad \text{(Eq1)}$$

Where Amb represents ambient HFA-134a levels; $A_1$, $A_2$, and $A_3$ represent coefficient of the rate constant $L_1$, $L_2$, and $L_3$, respectively; $L_1$, $L_2$, and $L_3$ are rate constant in units of reciprocal minutes; their corresponding half-lives can be computed by $-0.693/L_1$, $-0.693/L_2$, and $-0.693/L_3$. The calculated half-lives are 0.97, 20.7, and 442 minutes for subject #1 and 0.92, 27.6, and 355 minutes for subject #2.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

As used herein, "HFA-134(a)" means hydrofluoroalkane 1,1,1,2-tetrafluoroethane.

As disclosed herein, the inventors have developed a means of determining compliance and treatment efficacy with inhalers such as those used by asthmatics. In one embodiment, the present invention provides 1) analytical technique to measure 1,1,1,2-tetrafluoroethane gas (the most commonly used hydrofluoroalkane (HFA) in the inhaler's propellant) in a patient's breath in a range of parts-per-million (ppbv) to parts-per-trillion (pptv) using gas chromatography and mass spectrometry and 2) multi-compartmental analysis of HFA bio-transport in the human airway following inhaled doses of ICS to estimate HFA elimination pharmacokinetic parameters such as rate constants. The measured breath HFA levels and estimated parameters can be used to investigate inhaler compliance and treatment efficacy.

In one embodiment, the invention provides a non-invasive method to determine compliance and treatment efficacy with inhalers such as those used by asthmatics. In one embodiment, a key aspect of this invention is to examine hydrofluoroalkane (HFA, the inhaler's aerosol propellant) in the exhaled human breath as a potential biomarker of asthma inhaler compliance.

In another embodiment, the present invention provides two main components: 1) analytical technique to measure breath HFA in a range of parts-per million (ppbv) to parts-per trillion (pptv) using gas chromatography and mass spectrometry and 2) multi-compartmental analysis of HFA bio-transport in the human airway following inhaled doses of ICS to estimate HFA elimination pharmacokinetic parameters such as rate constants. The measured breath HFA levels and estimated parameters can be used to investigate inhaler compliance and treatment efficacy. For example, HFA elimination parameters can be used to determine steady state HFA levels with repeated inhaler usage.

In another embodiment, the present invention utilizes HFA because 1) HFA is the most commonly used volatile aerosol propellant (CFC alternative since 1996) in metered dose inhalers to effectively deliver asthma medication to the lung, and 2) HFA is mainly eliminated by exhalation.

In another embodiment, the invention presents unique precision of breath HFA levels as low as parts-per-trillion (pptv), far exceeding previously reported HFA levels found either by the manufacturers or in the literature. This HFA detection levels are not yet available commercially.

As further described herein, inhaled corticosteroids (ICS) and β2-agonists are the primary pharmacotherapies of asthma management. However, suboptimal medication compliance is common in asthmatics and is associated with increased morbidity. In one embodiment, the present invention provides exhaled breath measurements of the aerosol used in the inhaled medications to be used as surrogate markers for asthma medication compliance. As further described herein, the inventors utilized ten healthy controls and randomly assigned to inhaled corticosteroids (Flovent HFA) or short acting bronchodilators (Proventil HFA). Both inhalers contain HFA-134(a) as aerosol propellant. Exhaled breath sampling and pulmonary function tests were performed prior to the inhaler medication dispersion, immediately after inhalation, then at 2, 4, 6, 8, 24, and 48 hours post administration. At baseline, mean (SD) levels of HFA-134a in the breath were 252 (156) pptv. Immediately after inhalation, HFA-134(a) breath levels increased to $300 \times 10^6$ pptv and were still well above ambient levels 24 hours post administration. The calculated ratio of forced expiratory volume in 1 s over forced vital capacity (FEV1/FVC) did not change over time following inhaler administration. Thus, breath HFA-134a levels can be used to assess inhaler medication compliance, as well as be used to evaluate how effectively the medicine is delivered.

In one embodiment, the present invention provides a method of determining the effectiveness of an inhaler medication, comprising taking a measurement of HFA-134(a) from an exhaled breath of an individual after the individual has inhaled a medication, and determining an effective administration of the medication based on the presence of a high level of HFA-134(a). In another embodiment, the individual is being treated for asthma. In another embodiment, the high level of HFA-134(a) is an at least $10^6$ order of magnitude increase relative to ambient levels of HFA-134(a).

In another embodiment, the present invention provides a device, comprising an analytic system that can take a measurement of HFA-134(a) from an exhaled breath of an individual after the individual has inhaled a medication, take a measurement and quantify a corresponding ambient level of HFA-134(a), and determine whether there has been an effective administration of the medication based on the presence of a high level of HFA-134(a) relative to the corresponding ambient level of HFA-134(a).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention.

One skilled in the art may develop equivalent means or reactants without the exercise of inventive capacity and without departing from the scope of the invention.

Example 1

Figure 1:
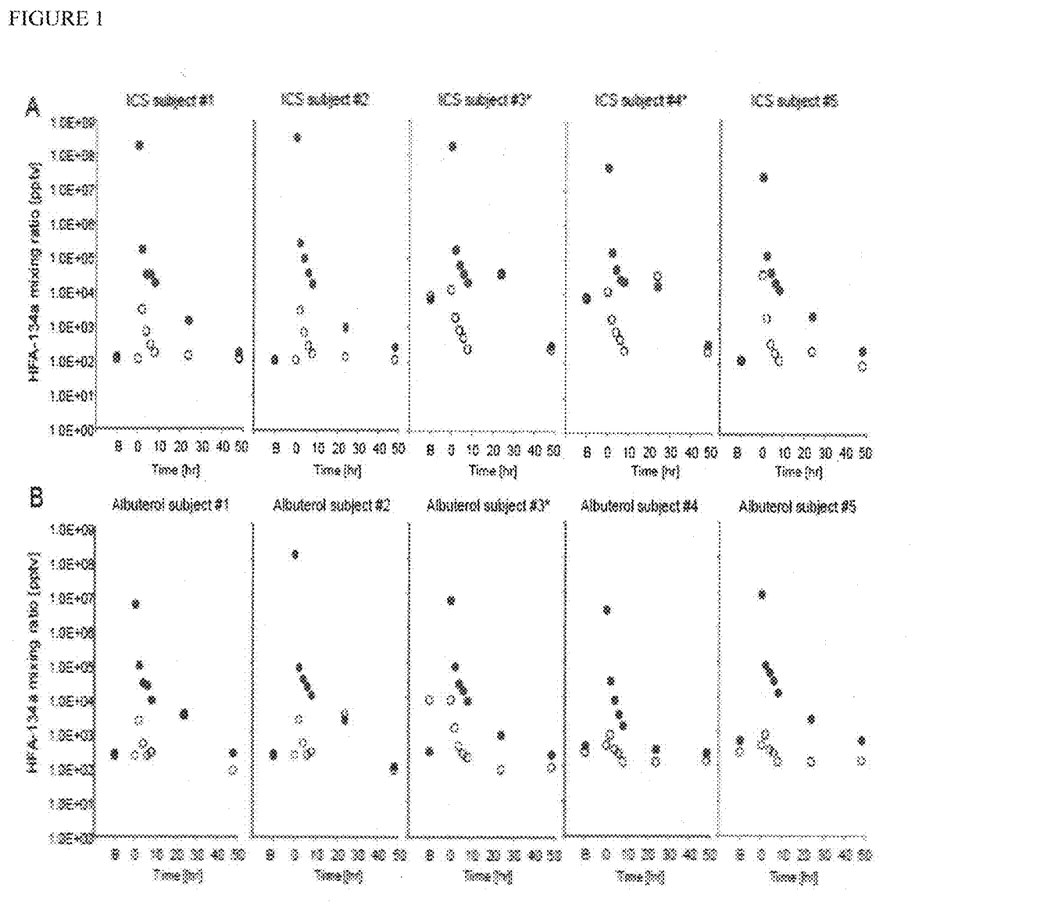
Figure 2:
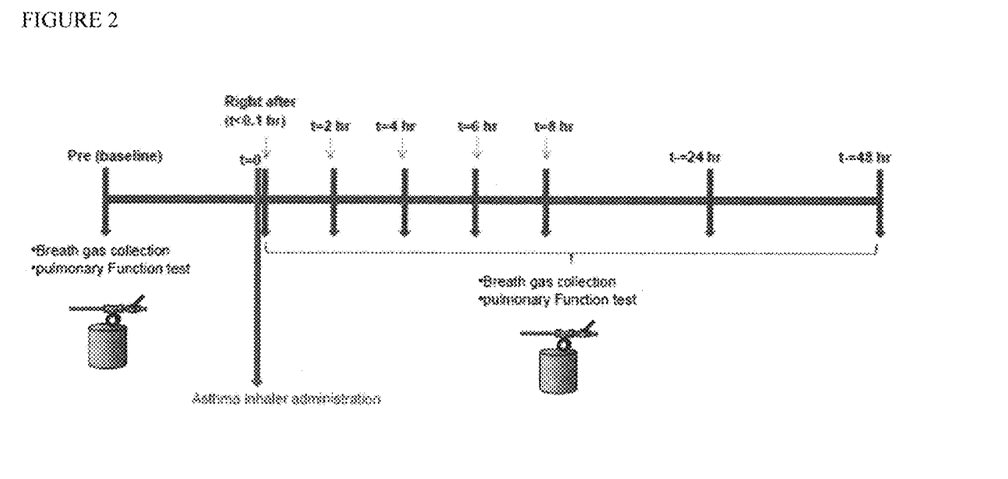
FIG. 2 depicts, in accordance with an embodiment herein, a timeline of the study.

As disclosed in FIGS. 1 and 2 herein, the inventors have built on accomplishments that demonstrate the feasibility of their approach. Briefly, that have collected and analyzed HFA levels in the exhaled breath of healthy controls (n=10, 25-48 yrs old) at baseline (prior to inhaler administration), immediately after (<5 min), 2 hr-post, 4 hr-post, 6 hr-post, 8 hr-post, 24 hr-post and 48 hr post inhaler administration. Two different asthma inhalers, Flovent HFA (corticosteroids inhaler) or Proventil HFA (albuterol bronchodilator) were used in the study to obtain basic pharmacokinetic information on HFA elimination in the lung who is naïve to HFA inhalers. As shown in FIGS. 1A and 1B, the preliminary observation demonstrated that the inventors can successfully detect HFA in the subject's breath and HFA concentration is still detectable at 48 hr post typical asthma inhaler administration, Breath HFA levels were also obtained from a symptomatic asthma subject who was on ICS (Flovent HFA), one puff per day for nine days prior to the study participation. As shown in FIG. 1C, baseline HFA level from a symptomatic asthma was 15-fold higher (710 ppt) when compared to the mean HFA levels obtained from ten 20 control participants (47 pptv).

Figure 5:
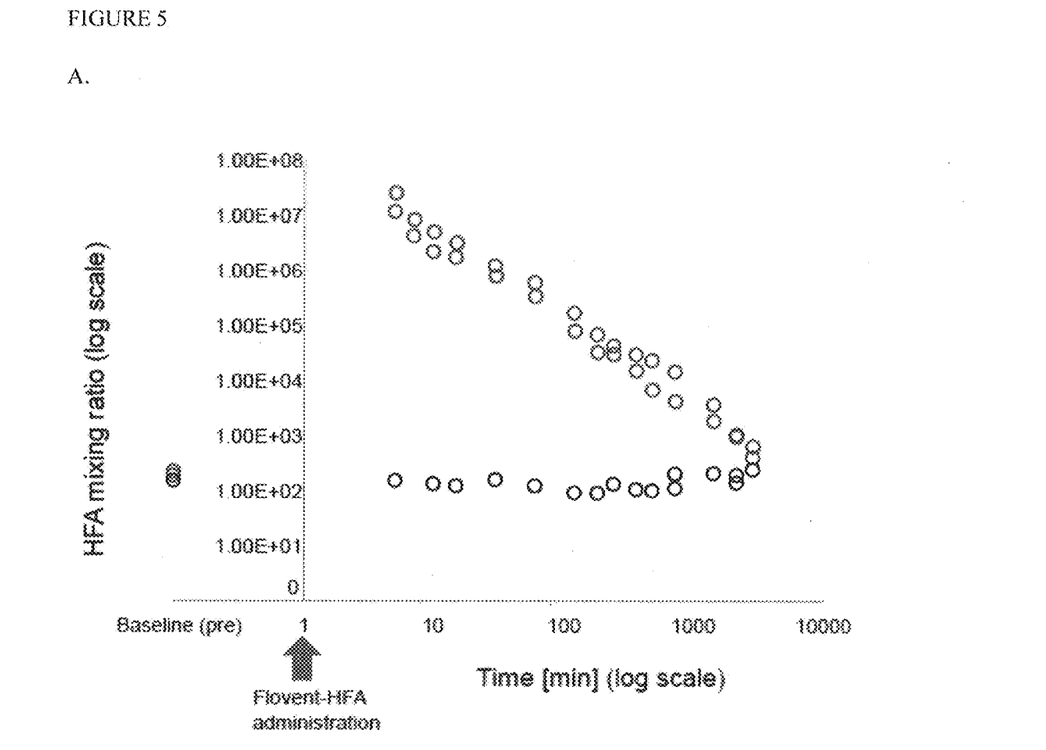
FIG. 5 depicts, in accordance with an embodiment herein, (A) HFA-134a levels (mixing ratios on log scale) in the exhaled breath of two healthy subjects at baseline, then, 5 min, 7 min, 10 min, 15 min, 30 min, 1 hr, 2 hr, 3 hr, 4 hr, 6 hr, 8 hr, 12 hr. 24 hr, 36 hr, and 48 hr—post Flovent HFA administration (red and blue open circle). All sample collections were held open space. The corresponding ambient air HFA-134a levels (open black circle) were ~150 pptv and did not change over time (B) HFA elimination parameters in healthy controls, where HFA elimination in the breath of healthy controls (n=2) follows 3-expoential decay expressed in Eq1. below.

As further disclosed in FIG. 5, the inventors re-defined the experiment and have performed a compartmental pharmacokinetic analysis of HFA elimination kinetics using HFA at 5 min, 7 min, 10 min, 15 min, 30 min, 1 hr, 2 hr, 3 hr, 4 hr, 6 hr, 8 hr, 12 hr. 24 hr, 36 hr, and 48 hr—post Flovent HFA administration. The HFA elimination could be modeled using three compartment pharmacokinetic analysis (Eq1).

$$C_{HFA-134a} = 1000(Amb + A_1 \cdot e^{(L_1 \cdot t)} + A_2 \cdot e^{(L_2 \cdot t)} + A_3 \cdot e^{(L_3 \cdot t)}) \quad \text{(Eq1)}$$

Where Amb represents ambient HFA-134a levels; $A_1$, $A_2$, and $A_3$ represent coefficient of the rate constant $L_1$, $L_2$, and $L_3$, respectively; $L_1$, $L_2$, and $L_3$ are rate constant in units of reciprocal minutes; their corresponding half-lives can be computed by $-0.693/L_1$, $-0.693/L_2$, and $-0.693/L_3$. The elimination rate constant in each compartment, $L_1$, $L_2$, and $L_3$, respectively are −0.1970, −0.0183, and −0.0013 for subject #1 and −0.1720, −0.0142, and −0.0018 for subject #2. The corresponding half-lives are 0.97, 20.7, and 442 minutes for subject #1 and 0.92, 27.6, and 355 minutes for subject #2.

Example 2

Advantages

In accordance with an embodiment herein, a key aspect of this invention is to use hydrofluoroalkane (HFA) in the exhaled human breath as a potential biomarker of asthma inhaler compliance. Breath HFA is attractive because 1) Breath HFA can be an objective measure of inhaler compliance because HFA is the most commonly used volatile aerosol propellant (CFC alternative since 1996) in metered dose inhalers to effectively deliver asthma medication to the lung 2) One can measure HFA concentration in the exhaled breath for at least 48 hours after a typical single inhalation, a useful interval in the clinical setting (See details above) 3) HFA is biologically inactive aerosol propellant, and is mainly eliminated by exhalation 4) It is non-invasive and allows for either real time detection or assessment later at a remote location 5) If the sample has been filtered during collection, it poses, unlike blood, little if any biohazard to healthcare workers or laboratory technicians.

In one embodiment, the invention presents unique precision of breath HFA levels as low as parts-per-trillion (pptv), far exceeding previously reported HFA levels found either by the manufacturers or in the literature. This HFA detection levels are not yet available commercially. The invention includes mathematical modeling of HFA elimination to establish appropriate compliance threshold and treatment efficacy window.

Example 3

Research

In one embodiment, the invention tests an innovative noninvasive approach utilizing HFA in the exhaled breath toward monitoring asthma inhaler compliance, and successfully demonstrates for the first time that 1) one can measure HFA concentration in the exhaled breath of healthy control participants and a symptomatic asthma subject and HFA concentration is still detectable at 48 hr post typical asthma inhaler administration, and 2) HFA elimination in the breath of control participants followed a three-compartment pharmacokinetic model.

In other embodiments, to relate breath HFA concentrations and estimated HFA elimination parameters with circulating levels of i) HFA and ii) active asthma medication (i.e., fluticasone); and B) To use exhaled breath biomarkers of drug metabolism. These gases will have a potential to be used as an adjunct to the breath HFA. To achieve these aims, the inventors recruit symptomatic and non-symptomatic asthma subjects, and measure breath HFA levels over time to estimate HFA elimination parameters using mathematical compartmental analysis. In another embodiment, the present invention provides a portable device that measures breath HFA levels as low as parts-per-trillion levels.

Example 4

Overview

Inhaled corticosteroids (ICS) and β2-agonists are the primary pharmacotherapies of asthma management. However, suboptimal medication compliance is common in asthmatics and is associated with increased morbidity. In one embodiment, the present invention provides exhaled breath measurements of the aerosol used in the inhaled medications to be used as surrogate markers for asthma medication compliance. As further described herein, the inventors utilized ten healthy controls and randomly assigned to inhaled corticosteroids (Flovent HFA) or short acting bronchodilators (Proventil HFA). Both inhalers contain HFA-134a as aerosol propellant. Exhaled breath sampling and pulmonary function tests were performed prior to the inhaler medication dispersion, immediately after inhalation, then at 2, 4, 6, 8, 24, and 48 hours post administration. At baseline, mean (SD) levels of HFA-134a in the breath were 252 (156) pptv. Immediately after inhalation, HFA-134a breath levels increased to 300×106 pptv and were still well above ambient levels 24 hours post administration. The calculated ratio of forced expiratory volume in 1 s over forced vital capacity (FEV1/FVC) did not change over time following inhaler administration. Thus, breath HFA-134a levels can be used to assess inhaler medication compliance, as well as be used to evaluate how effectively the medicine is delivered.

Example 5

Methods and Results

Subjects
Ten healthy subjects (5 males and 5 females, 25-48 years) participated in this study. Any subject with a history of any chronic medical conditions such as asthma, subjects with ongoing respiratory infection, food allergy and eczema, current smokers, users of other medications that contain HFA-134, or users of any prescription medication were excluded from the study. Female subjects with pregnancy/childbearing potential were excluded because there may be risks associated with asthma inhalers (16; 17). Pregnancy or child bearing potential status was requested from subjects via self-report at the time of enrollment. The Institutional Review Board at the University of California, Irvine approved the study, and informed consent was obtained from all participants.

Figure 3:
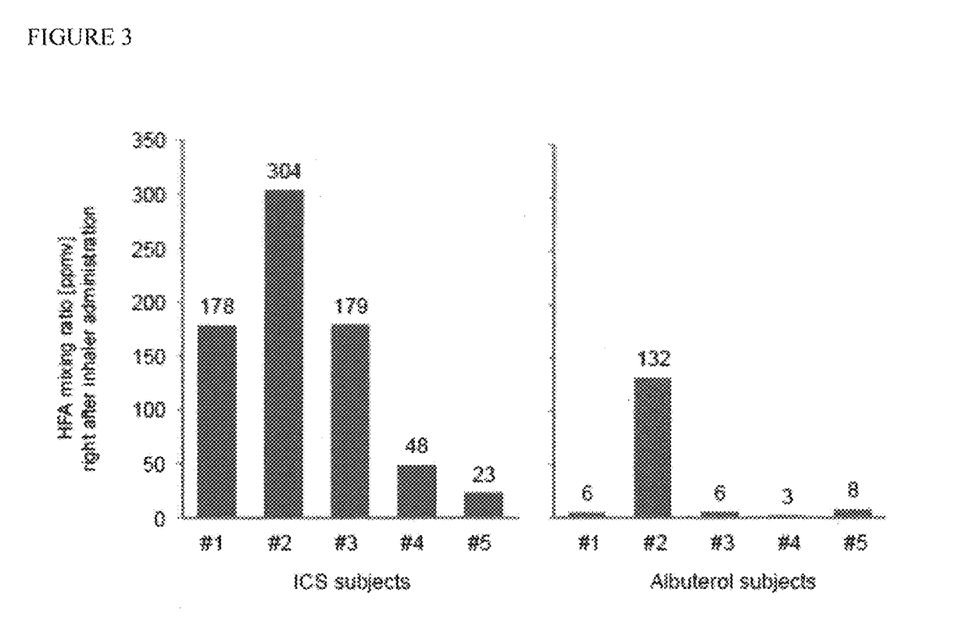
FIG. 3 depicts, in accordance with an embodiment herein, individual difference of breath HFA-134a levels (or mixing ratio) measured right after a typical single administration of Flovent HFA (red bar) or Proventil HFA (blue bar).

Protocol
Study participants were randomly assigned to inhaled corticosteroid (ICS, Flovent HFA, 220 mcg, n=5) or short acting bronchodilator (Albuterol, Proventil HFA, n=5). Baseline exhaled breath sampling and standard lung function test were performed prior to the medication dispersion. After baseline measurements, the participants inhaled two puffs of either Flovent HFA (Glaxo Smith Kline) or Proventil HFA (Merck & CO., INC) using a spacer (AeroChamberPlus Flow-Vu, Monaghan). Breath sampling and lung function test were performed immediately after inhalation (<5 min), and at 2, 4, 6, 8, 24, and 48 hours post administration (see FIG. 3).

Breath Sample Collection and Analysis
Exhaled breath samples were collected in evacuated electro-polished stainless steel canisters (volume=1.9 L). The analytic system used in this study is similar to the system described in Colman et al., 2001 (18). Briefly, 790 mL of the collected air sample is pre-concentrated in a stainless steel loop filled with glass beads and submerged in liquid nitrogen to remove the nitrogen, oxygen and argon present in the sample. The sample is re-vaporized using hot water (at approximately 80° C.) and split into five different column/detector combinations housed in three gas chromatographs (GCs) using UHP helium as the carrier gas: (1) DB-1 column (J&W; 60 m, 0.32 mm I.D., 1 μm film thickness) output to a flame ionization detector (FID); (2) DB-5 column (J&W; 30 m, 0.25 mm I.D., 1 vim film thickness) connected in series to a RESTEK 1701 column (5 m, 0.25 mm I.D., 0.5 μm film thickness) and output to an electron capture detector (ECD); (3) RESTEK 1701 column (60 m, 0.25 mm I.D., 0.50 μm film thickness) output to an ECD; (4) PLOT column (J&W GS-Alumina; 30 m, 0.53 mm I.D.) connected in series to a DB-1 column (J&W; 5 m, 0.53 mm I.D., 1.5 μm film thickness) and output to an FID; (5) DB-5 ms column (J&W; 60 m, 0.25 mm I.D., 0.5 μm film thickness) output to a quadrupole mass spectrometer detector (MSD, HP 5973). The MSD is set to operate in selected ion monitoring (SIM) mode with one ion chosen to quantify each compound in order to achieve the maximum selectivity and to avoid potential interferences. All gas chromatographs and detectors used in this study are manufactured by Hewlett Packard. The analytical system allows for the identification and quantification of different classes of volatile organic compounds (VOCs). HFA-134a levels in the breath samples were detected and quantified using the MSD (5% precision, 10% accuracy). Simultaneously, room air samples were also collected in the same location to quantify corresponding ambient levels of HFA-134a. HFA-134a levels are expressed as mixing ratio. The mixing ratio of HFA-134a is the ratio of the number density of HFA-134a to the total number density of air. Or, in other words, is the ratio of the number of molecule of HFA-134a in a unit volume to the number of molecule of air in a unit volume.

Pulmonary Function Test
A standardized pulmonary function test was performed in order to assess lung function in all subjects at baseline and post-medication administration. This test includes forced expiratory volume in 1 second (FEV1), calculated ratio of forced expiratory volume in 1 second to forced vital capacity (FEV1/FVC), and forced expiratory flow 25-75% ($FEF_{25-75}$).

Results

Ten subjects completed the study procedure without any complications, and no serious adverse events associated to the study were reported. The physical characteristics of the subjects are presented in Table 1.

Figure 4:
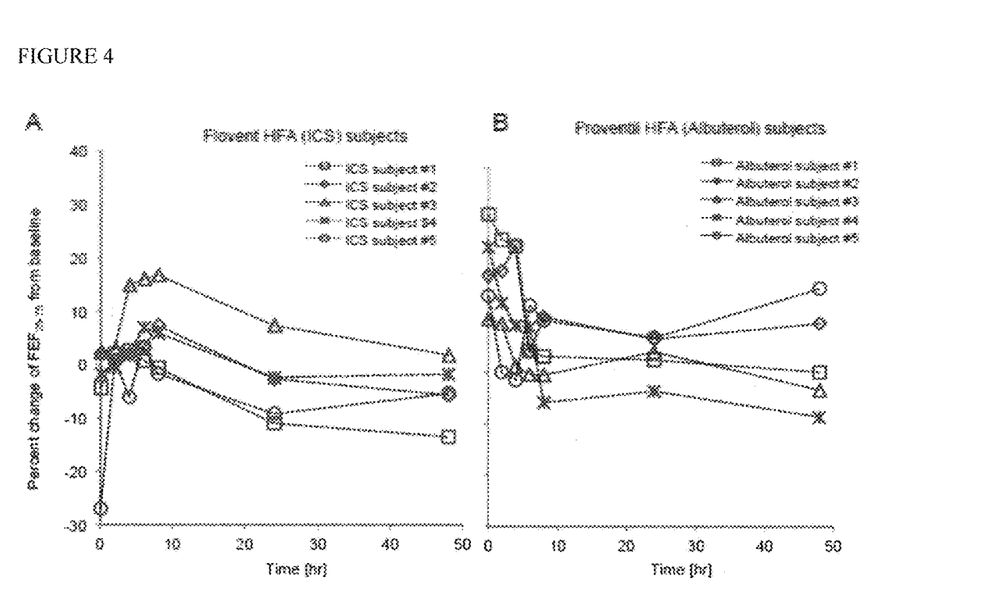
FIG. 4 depicts, in accordance with an embodiment herein, the percent change of FEF25-75 from baseline after (A) Flovent HFA and (B) Proventil HFA administration.

They successfully detected and quantified HFA-134a in all ten participants' exhaled breath at baseline (before applying asthma inhalers), right after inhaler administration, at 2, 4, 6, 8, and at 24 and 48 hour post typical asthma inhaler administration, a useful interval in the clinical setting (see FIGS. 4 and 5). They monitored breath carbon dioxide ($CO_2$) as a reference breath gas to ensure that the gas sampled was alveolar gas. The mean (standard deviation) $CO_2$ level was 4.1 (0.6) % of all breath samples.

Seven out of ten participants (ICS subjects #1, #2, and #5; Albuterol subjects #1, #2, #4, and #5 in FIG. 4) showed the following trend: trace levels of exhaled breath HFA-134a at baseline in the parts per trillion by volume (pptv) range, and then significantly higher levels, approximately 106 orders of magnitude (in the 3-300 part per million by volume, ppmv, range) after a typical single inhalation followed by a bi-exponential decaying pattern for at least 48 hours post inhalation. At baseline, mean (SD) levels of HFA-134a in the breath of these seven participants were 252 (156) pptv and the corresponding mean ambient HFA-134a levels in the room air were 178 (72) pptv. Exhaled breath HFA-134a levels went up to 3-300 ppmv right after inhalation (see FIG. 5) and then gradually decreased back to baseline levels. At 48-hr post inhaler administration, mean (SD) levels of HFA-134a in the exhaled breath were 260 (138) pptv. Corresponding HFA-134a levels in the ambient room air at 48-hr post inhaler administration were 111 (23) pptv.

Three participants presented higher exhaled breath and/or room HFA-134a levels either at baseline or during the 24-h time point (ICS subjects #3 and #4; Albuterol subject #3 in FIG. 4). Precisely, in inventors observed that the ambient room sample corresponding to the baseline time point for Albuterol subject #3 was particularly elevated (8320 pptv; FIG. 4B). However, breath HFA-134a time trend for this subject followed the same pattern observed for the previous seven subjects with a baseline breath HFA-134a value of 274 pptv, a right after medication level of 6.2 ppmv and a 48 hr post medication level of 224 pptv. The remaining two subjects (ICS subjects #3 and #4 in FIG. 4) showed particularly elevated levels of HFA-134a in the breath at baseline with 6350 and 7360 pptv, respectively (the corresponding room samples were elevated as well). However, for these two subjects the breath HFA-134a value reached right after drug administration was consistent with the general trend of the other subjects (179 and 48 ppmv, respectively) as well as the 48 hour time point (287 and 351 pptv).

As shown in Table 2, at baseline, mean (SD) of FEV1 (liter), FEV1/FVC (ratio), and FEF25-75 (liter/s) were 3.40 (0.89) and 3.46 (1.02); 0.84 (0.05) and 0.79 (0.05); 3.68 (1.05) and 3.15 (0.42) for Flovent HFA group and for Proventil HFA group, respectively. Mean (SD) of FEV1 and FEF25-75 percent predicted at baseline were 95 (4) % and 93 (15) %; 92 (12) % and 89 (9) % for Flovent HFA group and for Proventil HFA group, respectively. FEV1 and FEV1/FVC did not change significantly over time for both Flovent HFA group and Proventil HFA group while FEF25-75, an index of small airways obstruction changed more than 10% for both Flovent HFA group and Proventil HFA group. The percent change of FEF25-75 from baseline is presented in FIG. 6.

The study describes using a novel, non-invasive way to evaluate inhaler use by measuring in the exhaled breath the biologically inactive aerosol propellant HFA-134a present in asthma medications. The study demonstrated that one can successfully measure propellant HFA-134a levels in the human breath as low as parts-per-trillion for at least 48 hours after a typical single asthma inhaler administration.

The fate of propellant HFA-134a after the sustained exposure had previously been studied and it has been reported that HFA-134a is mainly eliminated by exhalation within the first few minutes after administration (24; 25). Gunnare et al., (19; 20) followed both plasma and breath HFA-134a levels from participants who were exposed in 500 ppm of HFA-134a for two hours. His study revealed that plasma HFA-134a concentration raises rapidly right after the 500 ppm of HFA-134a exposure, and maintained high levels during two hours of continued exposure period. The exhaled breath HFA-134a decreased almost an order of magnitude faster than HFA-134a in plasma when exposure stopped, and was not-detectable the day after the exposure. The rapid elimination of HFA-134a in the breath was also proved by measuring body retention rate using 18F-labeled HFA-134a (21; 22). Pike et al. (21) demonstrated that the 18F labeled HFA-134a was rapidly eliminated by ventilation during the first few minutes, and the body retention of remaining 18F-HFA-134a was below 10-15% at 5-10 minute from exposure from both healthy control subjects and patients with chronic airflow limitation. Furthermore, these studies revealed that 18F-HFA-134a was distributed throughout the body with no obvious accumulation in any specific region; and was not metabolized even after repeated dosing (21; 22). The only metabolite originating from HFA-134a was trifluoroacetic acid. However, trifluiriacetic acid was only detected in some urine samples at trace levels (i.e., less than 0.0005% of the administered dose) (23). Harrison et al., also reported that HFA-134a levels in blood samples decreased to below 10% of the initially administered concentration, and thus demonstrated that the removal of HFA-134a from the blood was rapid (24).

Unlike previous findings, the inventors have demonstrated the ability of detecting HFA-134a levels in the human breath in concentrations as low as parts-per-trillion. At baseline (before inhaler use) and at 48 hours post inhaler administration, breath HFA-134a levels were similar to the room HFA-134a levels (approximately 200 pptv). After two puffs of asthma inhaler administration, the breath HFA-134a levels varied between 3 and 300 ppmv (see FIG. 3). This wide range of breath HFA-134a concentrations measured right after inhalation may reflect individual differences in the ability of human beings to coordinate the complex maneuver required for successful inhalation. Additionally, there may be individual subject differences in HFA-134a transport and elimination in the airway mucosa, and/or dynamic changes of HFA-134a elimination that occur relatively in the early phases of HFA washout.

In many previous studies, investigators crucially failed to measure the ambient levels of the target VOC. The importance of this was illustrated in the present study. For all the participants, the 2-hr ambient HFA-134a concentration was always high. The room HFA-134a levels measured at baseline was between 109 and 254 pptv, consistent to the average level observed in the atmosphere. However, the HFA-134a levels in the room at the 2-hr time point ranged between 780 and 2960 pptv. Two different factors could be contributing to this room HFA-134a level enhancement, the first being the involuntary release of traces of HFA-134a inhalers in the room during the patient's drug administration. Additionally, the room air sample for the 2-hr time point could be affected by the extremely elevated levels of HFA-134a that the subject was exhaling in the exam room at this time point (28000-266000 pptv), and that have been exhaled when the asthma inhalers was administered 2 hours prior (3-300 ppmv).

The high levels of HFA-134a in the room samples measured for the baseline time point for Albuterol subject #3 could be the result of an unexpected HFA-134a emission in the exam room. Ambient levels decreased gradually for the subsequent time point reaching average ambient levels approximately at the 6-hr time point (FIG. 2). Finally, we note that high HFA-134a levels were measured for both breath and room samples for the baseline time point of ICS subjects #3 and #4 (FIG. 4A).

Figure 6:
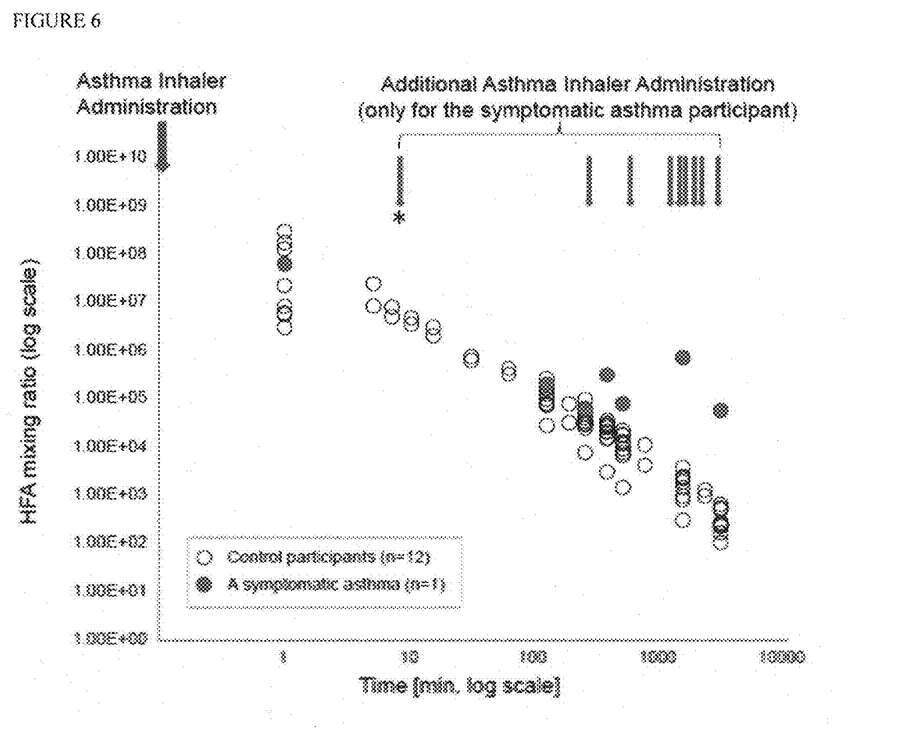
FIG. 6 depicts, in accordance with an embodiment herein, Control (n=12) vs. asthma (n=1): open circle represents breath HFA levels from healthy controls after a single asthma inhaler administration. Closed pink circle represents breath HFA from a symptomatic asthma who need additional asthma inhalers to control symptoms (pink arrows indicated additional inhaler administration) during 48 hours of the study duration.

As shown in FIG. 6, forced expiratory volume in one second (FEV1) and Forced expiratory volume in one second over forced vital capacity (FEV1/FVC) did not change significantly over time following inhaler administration for all ten healthy control participants. However, remarkably, we observed a substantial effect of both Flovent HFA and Proventil HFA on FEF25-75 in these control participants. FEF25-75 is an average forced expiratory flow during the mid (25-75%) portion of the forced vital capacity, and the reduction in FEF25-75 indicates a possible obstructive defect in small airways. The current study demonstrated that the short-acting bronchodilator (Proventil HFA) usage improves small airway obstruction or FEF25-75 immediately after administration; while inhaled corticosteroid usage (Flovent HFA) shows delayed responses, with an improved small airway obstruction recorded 4-8 hours after the Flovent HFA administration.

Conclusion

The inventors have demonstrated that 1) HFA-134a can be measured in the exhaled breath of healthy participants down to part per trillion levels; and 2) the HFA may be detectable above ambient levels for up to 24 hours following an inhalation. Breath HFA-134a is an important biomarker that can be used to determine inhaler medication compliance and/or as a tool to teach patients optimal ways to use the inhalers. There are currently two HFAs in use as propellants for asthma medication (HFA-134a and HFA-227) and these can be distinguished using GC-MS.

Example 6

TABLE 1

Table 1 - Physical characteristic of study participants Characteristic

| | | |
|---|---|---|
| Assigned Asthma inhaler | Flovent HFA-134A | Proventil HFA-134A |
| Age (yr), mean (range) | 29 (26-37) | 41 (32-48) |
| Male/Female, No. | 2/3 | 3/2 |
| BMI, mean (range) | 23.8 (21.1-26.6) | 21.8 (18.7-25.7) |

(BMI = body mass index)

Example 7

TABLE 2

Summary of pulmonary function test

| Participants | | Mean % change from baseline | | | | | | |
|---|---|---|---|---|---|---|---|---|
| taking Flovent (n = 5) | Baseline | Immediately after | 2 hr | 4 hr | 6 hr | 8 hr | 24 hr | 48 hr |
| $FEV_1$, Liter | 3.40 | −0.56 | 1.32 | 1.96 | 1.86 | 0.96 | 0.62 | 0.78 |
| $FEV_1$/FVC, ratio | 0.84 | −1.68 | 0.66 | 0.96 | 1.78 | 1.08 | 0.24 | −0.26 |
| $FEF_{25-75}$, Liter/s | 3.68 | −5.68 | 1.3 | 3.1 | 6.14 | 5.62 | −3.5 | −4.82 |
| Participants | | Mean % change from baseline | | | | | | |
| taking Proventil (n = 5) | Baseline | Immediately after | 2 hr | 4 hr | 6 hr | 8 hr | 24 hr | 48 hr |
| $FEV_1$, Liter | 3.46 | 3.18 | 3.74 | 2.42 | 0.44 | 0.36 | −0.4 | −0.78 |
| $FEV_1$/FVC, ratio | 0.79 | 4.72 | 4.16 | 3.72 | 2.42 | 0.62 | 1.34 | 1.38 |
| $FEF_{25-75}$, Liter/s | 3.15 | 19.94 | 13.82 | 11.74 | 5.994 | 3.62 | 3.3 | 2.9 |

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Bloom B, Cohen R A, Freeman G. Summary health statistics for U.S. children: National Health Interview Survey, 2011. Vital Health Stat. 10 2012; (254):1-88.
2. Schiller J S, Lucas J W, Peregoy J A. Summary health statistics for U.S. adults: National Health Interview Survey, 2011. Vital Health Stat. 10 2012; (256):1-218.
3. National Hospital Ambulatory Medical CAre Survey: 2010 Emergency Department Summary Tablesm Table 12 Centers for Disease Control and Prevention. 2013.
4. National Hospital Discharge Survey: 2010 table, average length of stay and days of care Centers for Disease Control and Prevention. 2013.
5. Hawkins G, McMahon A D, Twaddle S, Wood S F, Ford I, Thomson N C. Stepping down inhaled corticosteroids in asthma: randomised controlled trial. BMJ 2003 May 24; 326(7399):1115.
6. Pedersen S, O'Byrne P. A comparison of the efficacy and safety of inhaled corticosteroids in asthma. Allergy 1997; 52(39 Suppl):1-34.
7. Apter A J, Wang X, Bogen D K, Rand C S, McElligott S, Polsky D, Gonzalez R, Priolo C, Adam B, Geer S, et al. Problem solving to improve adherence and asthma outcomes in urban adults with moderate or severe asthma: a randomized controlled trial. J. Allergy Clin. Immunol. 2011 September; 128(3):516-23.
8. Bender B, Milgrom H, Rand C. Nonadherence in asthmatic patients: is there a solution to the problem? Ann. Allergy Asthma Immunol. 1997 September; 79(3):177-85.
9. Onyirimba F, Apter A, Reisine S, Litt M, McCusker C, Connors M, ZuWallack R. Direct clinician-to-patient feedback discussion of inhaled steroid use: its effect on adherence. Ann. Allergy Asthma Immunol. 2003 April; 90(4):411-5.
10. Gamble J, Stevenson M, McClean E, Heaney L G. The prevalence of nonadherence in difficult asthma. Am. J. Respir. Crit Care Med. 2009 Nov. 1; 180(9):817-22.
11. Murphy A C, Proeschal A, Brightling C E, Wardlaw A J, Pavord I, Bradding P, Green R H. The relationship between clinical outcomes and medication adherence in difficult-to-control asthma. Thorax 2012 August; 67(8):751-3.
12. Suissa S, Ernst P, Kezouh A. Regular use of inhaled corticosteroids and the long term prevention of hospitalisation for asthma. Thorax 2002 October; 57(10):880-4.
13. Williams L K, Peterson E L, Wells K, Ahmedani B K, Kumar R, Burchard E G, Chowdhry V K, Favro D, Lanfear D E, Pladevall M. Quantifying the proportion of severe asthma exacerbations attributable to inhaled corticosteroid nonadherence. J. Allergy Clin. Immunol. 2011 December; 128(6):1185-91.
14. Patel M, Perrin K, Pritchard A, Williams M, Wijesinghe M, Weatherall M, Beasley R. Accuracy of patient self-report as a measure of inhaled asthma medication use. Respirology. 2013 April; 18(3):546-52.
15. Chan A H, Reddel H K, Apter A, Eakin M, Rickert K, Foster J M. Adherence monitoring and e-health: how clinicians and researchers can use technology to promote inhaler adherence for asthma. J Allergy Clin. Immunol. Pract. 2013 September; 1(5):446-54.
16. George J, Abramson M J, Walker S P. Asthma in pregnancy: are inhaled corticosteroids safe? Am. J Respir. Crit Care Med. 2012 Mar. 1; 185(5):476-8.
17. Tegethoff M, Greene N, Olsen J, Schaffner E, Meinlschmidt G. Inhaled glucocorticoids during pregnancy and offspring pediatric diseases: a national cohort study. Am. J Respir. Crit Care Med. 2012 Mar. 1; 185(5):557-63.
18. Colman J J, Swanson A L, Meinardi S, Sive B C, Blake D R, Rowland F S. Description of the analysis of a wide range of volatile organic compounds in whole air samples collected during PEM-tropics A and B. Anal Chem 2001; 73(15).
19. Gunnare S, Ernstgard L, Sjogren B, Johanson G. Toxicokinetics of 1,1,1,2-tetrafluoroethane (RFC-134a) in male volunteers after experimental exposure. Toxicol. Lett. 2006 Nov. 1; 167(1):54-65.
20. Gunnare S, Ernstgard L, Sjogren B, Johanson G. Experimental exposure to 1,1,1-trifluoroethane (HFC-143a): uptake, disposition and acute effects in male volunteers. Toxicol. Lett. 2007 August; 172(3):120-30.
21. Pike V W, Aigbirhio F I, Freemantle C A, Page B C, Rhodes C G, Waters S L, Jones T, Olsson P, Ventresca G P, Tanner R J, et al. Disposition of inhaled 1,1,1,2-tetrafluoroethane (HFA134A) in healthy subjects and in patients with chronic airflow limitation. Measurement by 18F-labeling and whole-body gamma-counting. Drug Metab Dispos. 1995 August; 23(8):832-9.
22. Ventresca G P. Clinical pharmacology of HFA134a. J. Aerosol Med. 1995; 8 Suppl 1:S35-S39.
23. Monte S Y, Ismail I, Mallett D N, Matthews C, Tanner R J. The minimal metabolism of inhaled 1,1,1,2-tetrafluoroethane to trifluoroacetic acid in man as determined by high sensitivity 19F nuclear magnetic resonance spectroscopy of urine samples. J Pharm. Biomed. Anal. 1994 December; 12(12): 1489-93.
24. Harrison L I, Donnell D, Simmons J L, Ekholm B P, Cooper K M, Wyld P J. Twenty-eight-day double-blind safety study of an HFA-134a inhalation aerosol system in healthy subjects. J. Pharm. Pharmacol. 1996 June; 48(6): 596-600.

What is claimed is:

1. A method of determining the effectiveness of an inhaler medication, comprising:
    taking a measurement of HFA-134(a) from an exhaled breath of an individual after the individual has inhaled a medication;
    determining an effective administration of the medication based on the presence of a high level of HFA-134(a).

2. The method of claim 1, wherein the individual is being treated for asthma.

3. The method of claim 1, wherein the medication is a corticosteroid.

4. The method of claim 1, wherein the medication is a short acting bronchodilator.

5. The method of claim 1, wherein the medication is Flovent HFA or Proventil HFA.

6. The method of claim 1, wherein the medication is a β2 agonist.

7. The method of claim 1, wherein the measurement of HFA-134(a) is taken within 24 hours of inhaling the medication.

8. The method of claim 1, wherein the measurement of HFA-134(a) is taken between 5 and 12 hours of inhaling the medication.

9. The method of claim 1, wherein the measurement of HFA-134(a) is taken between 24 and 48 hours of inhaling the medication.

10. The method of claim 1, wherein the high level of HFA-134(a) is at or above $300 \times 10^6$ pptv HFA-134(a) levels.

11. The method of claim 1, wherein the high level of HFA-134(a) is an at least $10^6$ order of magnitude increase relative to normal levels.

12. The method of claim 1, wherein the high level of HFA-134(a) is an at least $10^3$ order of magnitude increase relative to ambient levels of HFA-134(a).

13. The method of claim 1, wherein the high level of HFA-134(a) is an at least $10^2$ order of magnitude increase relative to ambient levels of HFA-134(a).

14. The method of claim 1, wherein the high level of HFA-134(a) is between 3 to 300 ppmv from measurements taken immediately after inhaling the medication.

15. The method of claim 1, wherein the high level of HFA-134(a) is about 260 pptv or more in exhaled breath.

16. The method of claim 15, wherein the measurement of HFA-134(a) in exhaled breath is taken within 48 hours of inhaling the medication.

17. A device, comprising:
    an analytic system that can take a measurement of HFA-134(a) from an exhaled breath of an individual after the individual has inhaled a medication,
    take a measurement and quantify a corresponding ambient level of HFA-134(a), and
    determine whether there has been an effective administration of the medication based on the presence of a high level of HFA-134(a) relative to the corresponding ambient level of HFA-134(a).

18. The device of claim 17, wherein the HFA-134(a) levels are measured and quantified using a mass spectrometer detector (MSD).

19. The device of claim 17, further comprising gas chromatography and mass spectrometry.

20. A method to determine compliance and treatment efficacy with inhalers, comprising examining hydrofluoroalkane (HFA) in the exhaled human breath as a biomarker of asthma inhaler compliance.

21. The method of claim 20, further comprising two components: 1) analytical technique to measure breath HFA in a range of parts-per-million to parts-per-trillion (pptv) using gas chromatography and mass spectrometry and 2) multi-compartmental analysis of HFA biotransport in the human airway following inhaled doses of ICS to estimate HFA elimination pharmacokinetic parameters such as rate constants.

* * * * *